US00PP18823P2

(12) United States Plant Patent
Klaveren

(10) Patent No.: US PP18,823 P2
(45) Date of Patent: May 20, 2008

(54) ***HYDRANGEA* PLANT NAMED 'BLUE HEAVEN'**

(50) Latin Name: *Hydrangea macrophylla*
Varietal Denomination: Blue Heaven

(76) Inventor: Arie D. Klaveren, Hoofdweg 149, De Kwakel (NL), 1424 PE ( * ) Notice: Subject to any disclaimer, the term of this patent is extended or adjusted under 35 U.S.C. 154(b) by 6 days.

(21) Appl. No.: 11/508,681

(22) Filed: Aug. 23, 2006

(51) Int. Cl.
*A01H 5/00* (2006.01)

(52) U.S. Cl. ..... Plt./250

(58) Field of Classification Search ..... Plt./250
See application file for complete search history.

*Primary Examiner*—Anne Marie Grunberg
*Assistant Examiner*—June Hwu
(74) *Attorney, Agent, or Firm*—Penny J. Aguirre

(57) ABSTRACT

A new cultivar of *Hydrangea macrophylla* named 'Blue Heaven' that is characterized by its very early spring blooming habit, its ability to re-bloom on new growth after deadheading, its consistently well formed, large sized inflorescences that are red-purple in color (bluer in color depending with alkaline pH and sufficient aluminum levels), its strong flower stems, and its durable thick foliage.

2 Drawing Sheets

Genus/species: *Hydrangea macrophylla.*
Varietal denomination: 'Blue Heaven'.

BACKGROUND OF THE INVENTION

The present invention relates to a new and distinct cultivar of *Hydrangea macrophylla* and will be referred to hereafter by its cultivar name, 'Blue Heaven'. 'Blue Heaven' represents a new Bigleaf *Hydrangea,* a deciduous shrub grown for landscape use and for use as a potted plant.

'Blue Heaven' arose as a naturally occurring whole plant mutation in June 2001 in De Kwakel, The Netherlands. 'Blue Heaven' was selected as a single unique plant from amongst 250 seedlings that were derived from sown in 1999 from numerous open pollinated cultivars of *Hydrangea macrophylla.* The seeds collected from open pollination were combined into one seed lot, therefore the parentage of 'Blue Heaven' is unknown.

Asexual reproduction of the new cultivar was first accomplished by softwood stem cuttings in De Kwakel, The Netherlands in February 2002 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Blue Heaven' as a unique cultivar of *Hydrangea macrophylla.*

1. 'Blue Heaven' is a very early spring bloomer and removal of spent blooms results in repeat bloom from early April to October in The Netherlands.
2. 'Blue Heaven' has consistently well formed, large sized inflorescences that are red-purple in color but typical of *Hydrangea macrophylla,* are bluer in color depending with alkaline pH and sufficient aluminum levels.
3. 'Blue Heaven' exhibits foliage that is thick in substance.
4. 'Blue Heaven' exhibits very strong stems.

5. 'Blue Heaven' is hardy at least to U.S.D.A. Zone 6.

The new cultivar of *Hydrangea* can be compared to *Hydrangea macrophylla* 'Blaumeise' (not patented) which is similar in foliage characteristics, however 'Blaumeise' has Lacecap type inflorescences whereas 'Blue Heaven' has Hortensia type inflorescences. 'Blue Heaven' can also be compared to *Hydrangea macrophylla* 'Renate Steinegger' (not patented), a cultivar with similar flowers in form and color, however 'Blue Heaven' has larger flowers, stronger stems, and thicker leaves.

BRIEF DESCRIPTION OF THE DRAWINGS

The photographs in the figures were taken of a one year-old plant of 'Blue Heaven' as grown outdoors in a 15 cm container in De Kwakel, The Netherlands.

The photograph on the first sheet illustrates a plant of 'Blue Heaven' in bloom.

The photograph of the top of the second sheet is a close-up view of a fully open inflorescence and the photograph on the bottom of the second sheet is a close-up view of a leaf of 'Blue Heaven'.

The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of a one year-old plants of the new cultivar as grown in 15 cm containers under ambient light, outdoors in De Kwakel, The Netherlands. Phenotypic differences may be observed with variations in environmental, climatic, and cultural conditions. The color determination is in accordance with the 2001 R.H.S. Colour Chart of The Royal Horticultural Society, London, England, except where general color terms of ordinary dictionary significance are used.

Botanical classification: 'Blue Heaven' is a cultivar of *Hydrangea macrophylla.*

Commercial classification: Bigleaf hydrangea. Hortensia type.

Parentage: *Hydrangea macrophylla,* the exact seed and pollen parent are unknown.

General description:

*Blooming period.*—Early spring blooming, removal of spent blooms results in repeat bloom from early April to October in The Netherlands.

*Plant habit.*—Broadly upright, deciduous shrub.

*Height and spread.*—Reaches about 45 cm in height and 30 cm in width when mature.

*Cold hardiness.*—At least to U.S.D.A. Zone 6, colder zones have not been tested.

*Heat tolerance.*—Known to tolerate temperatures of at least 32° C.

*Culture.*—Grows best in moist but well-drained, humus-rich soil in full sun or partial shade with protection from high winds.

*Diseases resistance.*—No susceptibility or resistance diseases known to effect *H. macrophylla* has been observed.

*Root description.*—Fine.

Growth and propagation:

*Propagation.*—Softwood stem cuttings.

*Time required for root development.*—About 3 weeks to fully develop in a liner as grown under greenhouse conditions at an average temperature of 20° C.

*Time required to produce a salable crop.*—About 12 months from propagation to a flowering plant in a 15 cm container.

*Growth rate and vigor.*—Moderate, growth rate is about 12 cm per month in spring.

Stem description:

*Stem shape.*—Round, solid.

*Stem strength.*—Very strong.

*Stem color.*—144A to 144B.

*Stem size.*—Average of 20.6 cm (to base of inflorescence), average of 4.5 mm in width.

*Stem surface.*—Glabrous, slightly glossy, sparsely covered with lenticels; about 5 per square cm, about 2 mm in length and 0.5 mm in width and 183A in color.

*Internode length.*—Average of 7.1 cm.

*Branching.*—A single dormant stem will produce an average of 4 lateral branches, sublateral branching is determined by pinching; 2 stems develop per pinched node.

Foliage description:

*Leaf shape.*—Ovate to broadly ovate to elliptic.

*Leaf arrangement.*—Opposite.

*Leaf division.*—Simple.

*Leaf number.*—Average of 8 (4 pairs) per lateral branch.

*Leaf base.*—Obtuse.

*Leaf apex.*—Acute.

*Leaf margins.*—Serrated.

*Leaf venation.*—Penninerved, recessed on upper surface, color 144D on upper surface and 144B on lower surface.

*Leaf size.*—Average of 11.9 cm in length and 8 cm in width.

*Leaf attachment.*—Petiolate.

*Leaf surface.*—Glabrous on upper and lower surface, slightly glossy on upper surface.

*Leaf color.*—Young foliage upper surface; 141A to 143A, young foliage lower surface; 144A to 146C, mature foliage upper surface; 137A to 139A, mature foliage lower surface; 138A.

*Petioles.*—Average of 2 cm in length and 4 mm in width, 144B in color.

Inflorescence description:

*Inflorescence type.*—Terminal compound globous corymb of rotate shaped flowers, about 70% of the flowers are sterile.

*Lastingness of inflorescence.*—Persistent but color is retained for about 4 weeks.

*Inflorescence number.*—One per lateral or sublateral stem if pinched.

*Inflorescence size.*—Average of 12.5 cm in height and 19.4 cm in diameter.

*Flower number.*—Numerous, average of 143 sterile flowers and 60 fertile flowers per inflorescence.

*Flower durability to stress.*—High.

*Flower fragrance.*—None.

*Time required to develop an inflorescence.*—Approximately 9 weeks after growth emerges when container grown.

*Flower aspect.*—Outward to upright.

*Flower size.*—Sterile flowers; average of 5 cm in diameter and 2.3 cm in depth, fertile flowers; average of 1 cm in diameter and 7 mm in depth.

*Flower buds.*—Average of 6 mm in length and 5 mm in width prior to opening, broadly ovate in shape, 76B to 76C in color, flowers open in about 3 days from mature bud.

*Peduncles.*—Strong, average of 6.5 cm in length and 1 mm in width on sterile flowers and an average of 4.5 cm in length and 0.8 mm in width on fertile flowers, held at about a 40° angle from vertical, 145B to 145C in color, surface is glabrous and shiny.

*Pedicels.*—Moderate strength, average of 2.2 cm in length and 4 mm in width, held at about a 15 to 20° angle from vertical, 64D in color, surface is glabrous and shiny.

*Calyx.*—Campanulate in form, average of 3.5 cm in length and 4 mm in diameter.

*Petals.*—Average of 5, present on fertile flowers only, rotate in arrangement, ovate in shape, entire margin, acute apex, cuneate base, average of 1.2 mm in length and 1 mm in width, surface is glabrous and dull on both surfaces, color of upper and lower surface (opening and mature flowers) is 144D with apex 144B to 144C.

*Sepals.*—Average of 4 for sterile flowers, average of 5 for fertile flowers, unfused, rotate in arrangement, glabrous and dull surface (both surfaces), orbicular in shape on sterile flowers, ovate in shape on fertile flowers, entire margin, apex is acute to rounded on sterile flowers and acute on fertile flowers, size on sterile flowers; average of 2.6 cm in length and 2.7 cm in width, size on fertile flowers; average of 4.6 mm in length and 2 mm in width, color on sterile flowers when flower opens upper surface; 64C and 64B near base, color on fertile flowers when flower opens upper surface; 76B to 76C, color on sterile flowers when flower opens lower surface; 64D color on fertile flowers when flower opens lower surface; 70C, color on sterile flowers when flower is fully open upper surface; 70B, color on fertile flowers when flower is fully open upper surface; 76B to 76C, color on sterile flowers when flower is fully open lower surface; 70C with slightly more reddish veins, color on fertile flowers when flower is fully open lower surface; 70C, petals fade to a brownish color 164D.

Reproductive organs: (fertile flowers):

*Stamens.*—Average of 10, anther is kidney shaped, about 1 mm in length and 9B in color, filament is an average of 3.5 mm in length and whiter than 155D in color, pollen is low in quantity and 158D in color.

*Pistils.*—Average of 3, average of 2 mm in length, stigma is club-shaped and 157A in color, style is an average of 1.2 mm in length and 70D in color, ovary is inferior and 145D to lighter in color.

*Fruit and seed.*—Has not been observed under the conditions tested to date.

I claim:

1. A new and distinct cultivar of *Hydrangea* plant named 'Blue Heaven' substantially as herein illustrated and described.

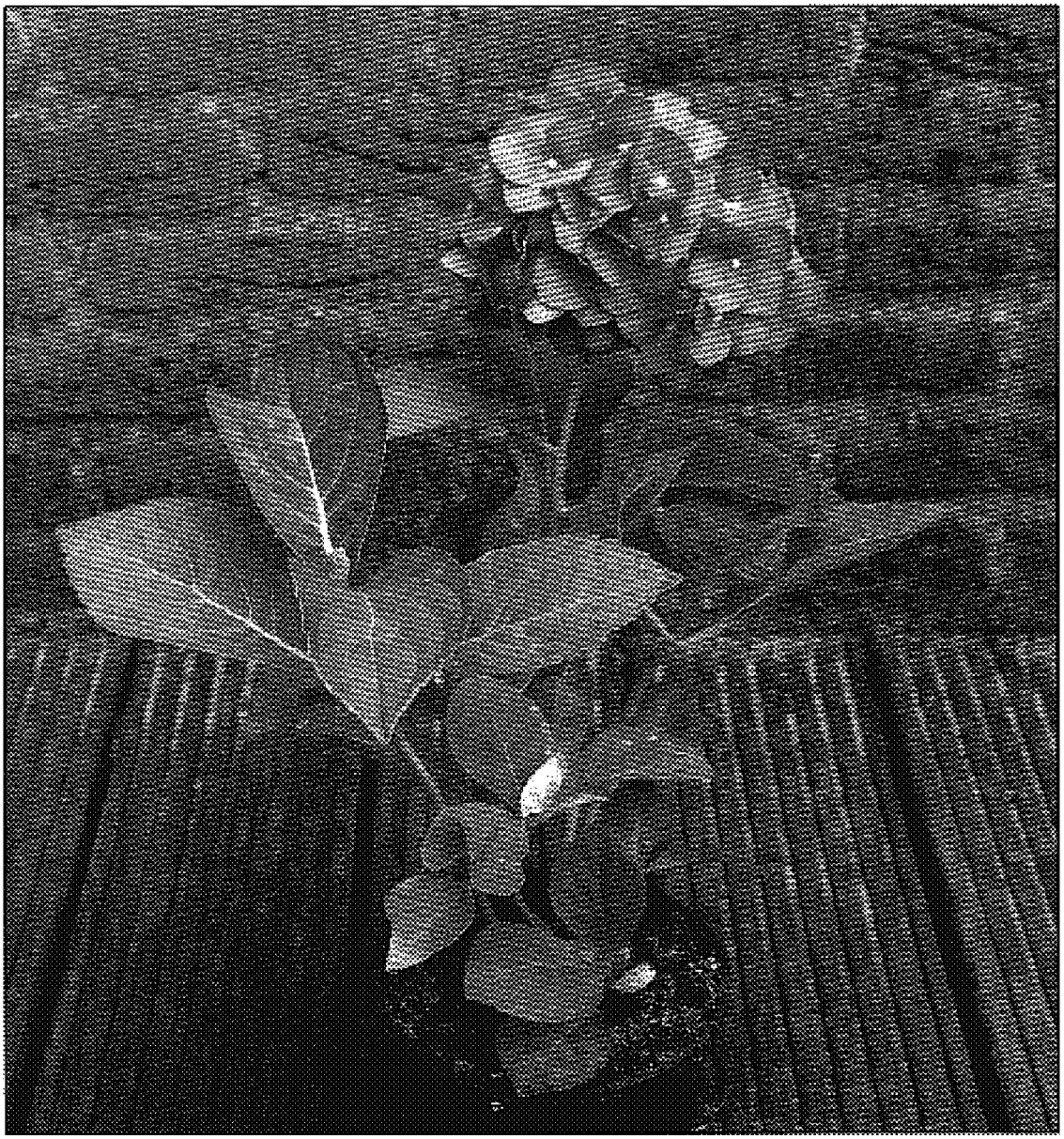

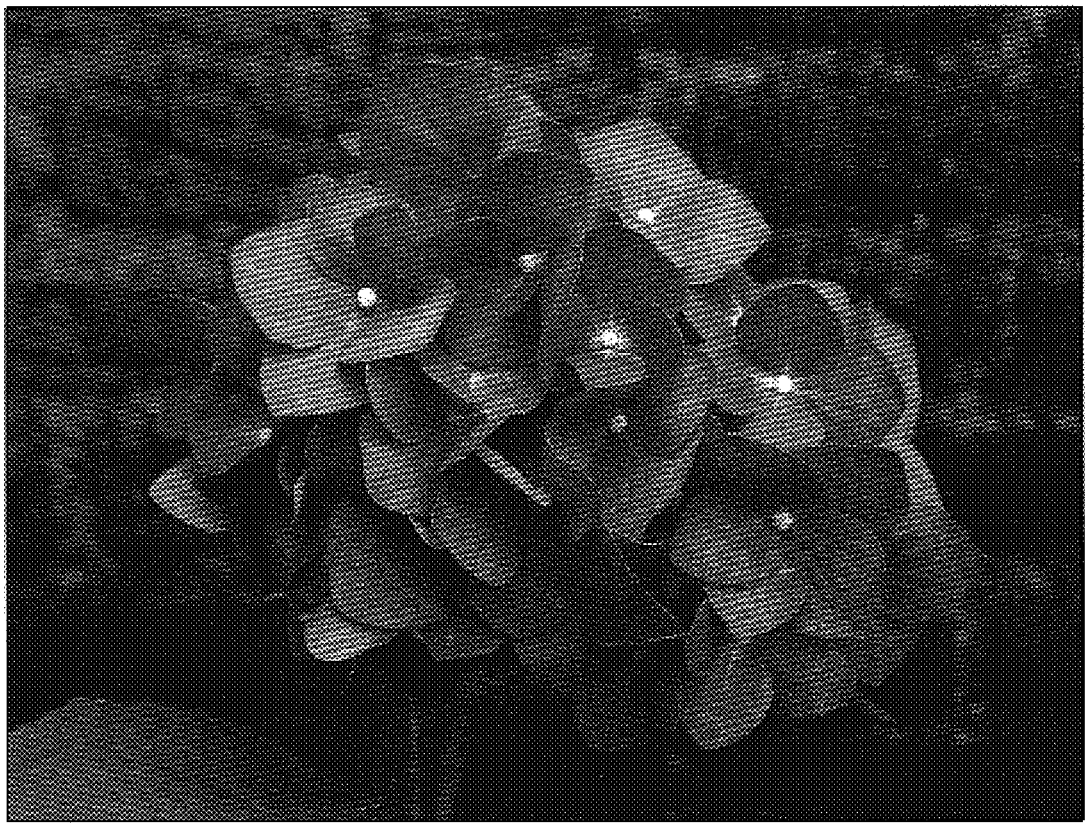
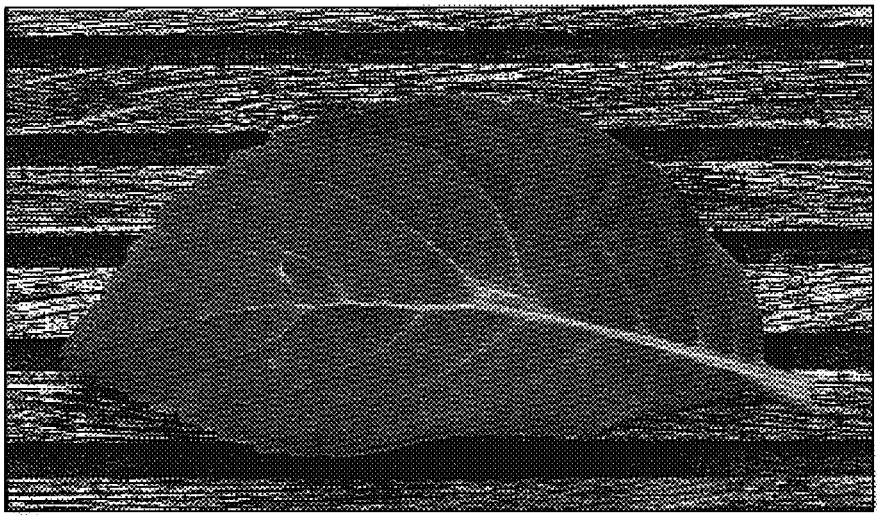

* * * * *